United States Patent
Xu et al.

(10) Patent No.: US 10,761,092 B2
(45) Date of Patent: Sep. 1, 2020

(54) MULTI-FLUX MICRO-FLUIDIC CHIP BASED ON ACTIVE FLUID FLOW CONTROL

(71) Applicant: NANJING LANSION BIOTECHNOLOGY CO., LTD., Nanjing, Jiangsu (CN)

(72) Inventors: Xingshang Xu, Jiangsu (CN); Jeffery Chen, Jiangsu (CN); Long Wang, Jiangsu (CN); Weiyan Sun, Jiangsu (CN); Qilu Wan, Jiangsu (CN); Shen Yang, Jiangsu (CN)

(73) Assignee: LANSION BIOTECHNOLOGY CO., LTD., Nanjing (CN)

( * ) Notice: Subject to any disclaimer, the term of this patent is extended or adjusted under 35 U.S.C. 154(b) by 0 days.

(21) Appl. No.: 16/079,516

(22) PCT Filed: Dec. 6, 2017

(86) PCT No.: PCT/CN2017/114690
§ 371 (c)(1),
(2) Date: Aug. 23, 2018

(87) PCT Pub. No.: WO2019/006977
PCT Pub. Date: Jan. 10, 2019

(65) Prior Publication Data
US 2019/0137488 A1    May 9, 2019

(30) Foreign Application Priority Data
Jul. 3, 2017 (CN) .......................... 2017 1 0531302

(51) Int. Cl.
*G01N 33/558* (2006.01)
*B01L 3/00* (2006.01)
*F16K 99/00* (2006.01)
*G01N 33/543* (2006.01)

(52) U.S. Cl.
CPC .......... *G01N 33/558* (2013.01); *B01L 3/5027* (2013.01); *B01L 3/50273* (2013.01); *B01L 3/502738* (2013.01); *B01L 3/502746* (2013.01); *F16K 99/0042* (2013.01); *G01N 33/54393* (2013.01); *B01L 2200/10* (2013.01); *B01L 2300/069* (2013.01); *B01L 2300/0861* (2013.01); *B01L 2300/0864* (2013.01); *B01L 2300/0867* (2013.01); *B01L 2300/0874* (2013.01); *B01L 2300/0887* (2013.01); *B01L 2400/0487* (2013.01); *B01L 2400/0655* (2013.01); *B01L 2400/082* (2013.01); *B01L 2400/084* (2013.01)

(58) Field of Classification Search
None
See application file for complete search history.

(56) References Cited

U.S. PATENT DOCUMENTS

| | | | | |
|---|---|---|---|---|
| 6,007,690 A | * | 12/1999 | Nelson | G01N 27/44791 204/450 |
| 6,062,261 A | * | 5/2000 | Jacobson | B01L 3/502 137/806 |
| 6,637,463 B1 | * | 10/2003 | Lei | 137/807 |
| 7,598,091 B2 | | 10/2009 | Wang | |
| 8,486,350 B2 | * | 7/2013 | Nakajima | B01L 3/502715 422/503 |
| 10,648,975 B2 | * | 5/2020 | Xu | G01N 33/558 |
| 2003/0044322 A1 | * | 3/2003 | Andersson | B01F 5/0646 422/506 |
| 2003/0070677 A1 | * | 4/2003 | Handique | B01F 5/0085 128/203.12 |
| 2003/0198576 A1 | | 10/2003 | Coyne et al. | |
| 2004/0037739 A1 | * | 2/2004 | McNeely | B01F 5/10 422/417 |
| 2004/0109793 A1 | * | 6/2004 | McNeely | B01F 5/0642 422/400 |
| 2007/0111302 A1 | * | 5/2007 | Handique | B01F 5/061 435/287.2 |
| 2012/0178091 A1 | * | 7/2012 | Glezer | 435/6.12 |

(Continued)

FOREIGN PATENT DOCUMENTS

| | | |
|---|---|---|
| CN | 101795769 A | 8/2010 |
| CN | 103566984 A | 2/2014 |

(Continued)

OTHER PUBLICATIONS

EPO Search Report dated Apr. 26, 2019 for related European application EP17896325.

*Primary Examiner* — Ann Y Lam (57) ABSTRACT

Provided is a multi-flux micro-fluidic chip including a chip body. The chip body includes a fluid inflow cavity communicated with an external air path, reaction-quantification cavities, waste liquid cavities, and a fluid path distribution cavity disposed at a middle position of the chip body. The two or more reaction-quantification cavities are distributed on two sides of the fluid path distribution cavity in rows to form the first and second row of reaction-quantification cavities respectively; and they are communicated with a fluid outlet of the fluid path distribution cavity through fluid path branches, and a fluid inlet of the fluid path distribution cavity through fluid path branches, and a fluid inlet of the fluid path distribution cavity is communicated with a fluid outlet of the fluid inflow cavity and an external fluid path, which making it possible to detect multiple items simultaneously and greatly improving the flux of the micro-fluidic chip.

7 Claims, 8 Drawing Sheets

(56) References Cited

U.S. PATENT DOCUMENTS

2013/0029338 A1    1/2013   Jovanovich
2014/0038209 A1    2/2014   Shih et al.
2016/0361715 A1*  12/2016   Shi .................... B01L 3/50273
2019/0032114 A1*   1/2019   Trivedi ................ C12Q 1/686

FOREIGN PATENT DOCUMENTS

| CN | 203899622 U | 10/2014 |
| CN | 205127986 U | 4/2016 |
| CN | 205797240 U | 12/2016 |
| CN | 106902904 A | 6/2017 |
| CN | 106902905 A | 6/2017 |
| CN | 107225006 A | 10/2017 |
| EP | 1493487 A1 | 1/2005 |

\* cited by examiner

MULTI-FLUX MICRO-FLUIDIC CHIP BASED ON ACTIVE FLUID FLOW CONTROL

BACKGROUND OF THE INVENTION

Technical Field

The present invention relates to a micro-fluidic chip based on active fluid flow control, in particular to a multi-flux micro-fluidic chip.

Description of Related Art

As a stable and practical technique, lateral flow immunoassay is suitable for point-of-care testing (POCT) of various types or field service.

In an immunochromatographic reaction system, the coefficient of variation (CV) is large due to system factors, and consequentially, precise quantification cannot be achieved. Immunodiagnosis methods based on the micro-fluidic technology can effectively solve these problems.

Micro-fluidic includes passive micro-fluidic and active micro-fluidic, wherein passive micro-fluidic still relies on capillary force to achieve forward lateral chromatography of fluid. However, due to different viscosities of different samples and particularly whole blood samples, uniform fluid velocities are unavailable.

Active micro-fluidic can effectively solve the aforesaid problem and can provide forward thrust to make fluid evenly flow forwards, thereby avoiding test value discrepancies caused by different flow velocities.

Power for active micro-fluidic includes centrifugal force drive, electric wetting drive and pressure drive (electrolytic pumps, compressed air pumps, chemical decomposition pumps and direct pressure differential drive).

However, in order to control the fluid velocity at will, besides the thrust, valve control and backflow prevention measures for preventing backflow of fluid after pressure relief are also indispensable.

Please refer to the following patents in the prior art for chip manufacturing and application:

(1) CN203899622U Micro-fluidic Chip
(2) CN106353491A Micro-fluidic Beside Rapid Diagnosis Kit
(3) CN205941345U Micro-fluidic Chip for Biological Detection Patent (1) does not involve a mixing function which is a key function for mixing different fluids as well as fluids and solids (such as embedded freeze-drying reagents) of micro-fluidic chips.

Wherein, in Patent (2) and Patent (3), a fluid sample added into a chip is not quantified; however, in order to realize quantitative detection, the sample added into the chip and a reagent pre-stored in the chip must be quantified.

Monitoring of the accurate position of fluid flowing in the chip is involved in none of Patent (1), Patent (2) and Patent (3), which means that in these three aforesaid patents, the filling behavior of fluid in a passage or cavity in the chip is not monitored before the final detection result of the chip comes out.

In addition, existing chips are small in flux, and only one to three items of each chip can be detected at the same time.

BRIEF SUMMARY OF THE INVENTION

One objective of the present invention is to overcome the defects of the prior art by providing a multi-flux micro-fluidic chip based on active fluid flow control, which evenly divides one fluid path into multiple fluid path branches creatively, making it possible to detect multiple items at the same time, and greatly improving the flux of the micro-fluidic chip.

In order to achieve the above technical goals, the invention adopts the following technical proposal.

A multi-flux micro-fluidic chip based on active fluid flow control, including a chip body, wherein the chip body includes a fluid inflow cavity, reaction-quantification cavities and waste liquid cavities, and the fluid inflow cavity is communicated with an external air path; characterized in that the multi-flux micro-fluidic chip based on active fluid flow control further includes a fluid path distribution cavity disposed at a middle position of the chip body; the number of the reaction-quantification cavities is four or more, and the four or more reaction-quantification cavities are distributed on two sides of the fluid path distribution cavity in rows to form a first row of reaction-quantification cavities and a second row of reaction-quantification cavities respectively; and the reaction-quantification cavities are communicated with a fluid outlet of the fluid path distribution cavity through respective fluid path branches, and a fluid inlet of the fluid path distribution cavity is communicated with a fluid outlet of the fluid inflow cavity and an external fluid path.

As a further improvement of the present invention, the fluid inlet of the fluid path distribution cavity is communicated with either the fluid inflow cavity or the external fluid path through a fluid inflow mechanism; and the fluid inflow mechanism includes a sample fluid inflow passage, a sample slow flow passage, a distribution cavity fluid inflow passage, an external fluid slow flow passage and an external fluid inflow passage, wherein the sample fluid inflow passage and the external fluid inflow passage are ascending passages, the distribution cavity fluid inflow passage is a descending passage, a fluid inlet of the sample fluid inflow passage is communicated with the fluid inflow cavity through a sample delivery passage, a fluid outlet of the sample fluid inflow passage is communicated with the fluid path distribution cavity sequentially through the sample slow flow passage and the distribution cavity fluid inflow passage, a fluid inlet of the external fluid inflow passage is communicated with the external fluid path through an external fluid delivery passage, and another end of the external fluid inflow passage is communicated with the fluid path distribution cavity sequentially through the external fluid slow flow passage and the distribution cavity fluid inflow passage.

As a further improvement of the present invention, the distribution cavity fluid inflow passage is formed by embedding a plug in a fluid inflow component groove including an isosceles triangle-shaped groove and a cylindrical outer sleeve, the isosceles triangle-shaped groove is reversely disposed, and the cylindrical outer sleeve is disposed along a center line of the isosceles triangle-shaped groove, starts from a bottom edge of the isosceles triangle-shaped groove and extends out of a vertex of the isosceles triangle-shaped groove, so that a circular fluid outflow duct of the distribution cavity fluid inflow passage is formed; the plug is provided with a cylindrical end cap matched with the cylindrical outer sleeve and symmetrically, with respect to a center line of the cylindrical end cap, provided with two oblique outer wall faces forming oblique fluid inflow passages respectively together with two equal oblique sides of the isosceles triangle-shaped groove; and one said oblique fluid inflow passage is communicated with the sample slow flow passage, and the other said oblique fluid inflow passage is communicated with the external fluid slow flow passage.

As a further improvement of the present invention, the fluid path distribution cavity is provided with a sample fluid inlet, an external fluid inlet and a plurality of fluid outlets, wherein the sample fluid inlet of the fluid path distribution cavity is communicated with the fluid inflow cavity through the sample delivery passage, the external fluid inlet of the fluid path distribution cavity is communicated with the external fluid path through the external fluid delivery passage, and the fluid outlets of the fluid path distribution cavity are communicated with the reaction-quantification cavities through the respective fluid path branches; and the fluid path branches are symmetrically distributed on two sides of a connecting line between the sample fluid inlet and the external fluid inlet of the fluid path distribution cavity, and each said fluid path branch has a passage width and a passage length in inverse proportion.

As a further improvement of the present invention, each said reaction-quantification cavity includes labeled antibody storage cavities and a coated antibody storage cavity, each said coated antibody storage cavity is disposed at a middle position of the corresponding reaction-quantification cavity and provided with a reaction pool fluid inflow branch and a reaction pool fluid outflow branch, and each of two sides of a connecting line between the reaction pool fluid inflow branch and the reaction pool fluid outflow branch of each said reaction-quantification cavity is provided with one said labeled antibody storage cavity.

As a further improvement of the present invention, a valve device is disposed on a micro-fluidic passage between each said reaction-quantification cavity and the corresponding waste liquid cavity includes:
- a detection mechanism used for sensing whether or not fluid flows through a valve device mounting position, a pressing mechanism and a sealing component;
- the valve devices in a normally open state in the chip body automatically close to be in an interruption state when numerical values fed back by the corresponding detection mechanisms indicate that fluid flows through the corresponding valve device mounting positions;
- the valve devices in the interruption state are regularly opened to be in a circulation state;
- when the valve devices are in the circulation state, fluid is pushed by air flow from the air path to circulate in the valve devices;
- each said sealing component is a conductive sealing ring and includes an outer sealing ring, an inner sealing film located on an inner ring of the outer sealing ring and a probe contact connected with the outer sealing ring;
- each said pressing mechanism includes a pressing head located above the corresponding inner sealing film;
- each said detection mechanism includes a detection probe which is in linking connection with the corresponding pressing head and located above the corresponding probe contact, and a distance from each said detection probe to the corresponding probe contact is smaller than a distance from each said pressing head to the corresponding inner sealing film;
- the micro-fluidic passage at each said valve device mounting position is transversely partitioned by a micro-fluidic passage partition into a micro-valve fluid inflow section and a micro-valve fluid outflow section;
- each said micro-valve fluid inflow section is provided with a fluid outlet, and each said micro-valve fluid outflow section is provided with a fluid inlet;
- each said inner sealing film is capable of covering the fluid outlet of the corresponding micro-valve fluid inflow section and the fluid inlet of the corresponding micro-valve fluid outflow section at the same time and is sealed by the corresponding outer sealing ring;
- when the pressing heads of the pressing mechanisms drive the detection probes to descend towards the conductive sealing rings, the pressing mechanisms stop descending when the detection probes make contact with the probe contacts, and at this moment, gaps exist between the pressing heads and the inner sealing films; when data sensed by the detection probes change, it indicates that fluid flows through the micro-fluidic passages at the valve device mounting positions, the pressing mechanisms are triggered to work to push the pressing heads to continue to descend till the pressing heads press against the inner sealing films to cover the fluid outlets of the micro-valve fluid inflow sections and the fluid inlets of the micro-valve fluid outflow sections at the same time, and the valve devices are in the interruption state at this moment; and
- when gaps exist between the pressing heads of the pressing mechanisms and the inner sealing films, the valve devices are in an open state, and as the inner sealing films are deformable, it is ensured that fluid flows out from the fluid outlets of the micro-valve fluid inflow sections and flows in from the fluid inlets of the micro-valve fluid outflow sections.

As a further improvement of the present invention, three said waste liquid cavities are separately disposed on a periphery of the chip body in a semi-enclosure mode and include a first waste liquid cavity, a second waste liquid cavity and a third waste liquid cavity, wherein the first waste liquid cavity and the second waste liquid cavity are located on two sides of the chip body, the third waste liquid cavity is communicated with the first waste liquid cavity and the second waste liquid cavity, the first waste liquid cavity is communicated with the first row of reaction-quantification cavities, and the second waste liquid cavity is communicated with the second row of reaction-quantification cavities.

As a further improvement of the present invention, the first waste liquid cavity and the second waste liquid cavity are of a same structure and each includes a waste liquid pool a, a middle cover plate a covering the waste liquid pool a and an upper cover plate a covering the middle cover plate a, each said middle cover plate a has a surface facing the corresponding waste liquid pool a and provided with an absorbent paper groove a for accommodating absorbent paper as well as a surface facing the corresponding upper cover plate a and provided with a plurality of conductive sealing ring grooves distributed at intervals, and the conductive sealing rings are disposed in the conductive sealing ring grooves; each said upper cover plate a is provided with capacitance probe penetration holes and pressing mechanism head penetration holes at positions corresponding to the conductive sealing ring grooves; a plurality of tooth-shaped flow guiding components are disposed on an inner wall face of each said waste liquid pool a at intervals, and absorbent paper positioning columns are disposed at positions close to tips of the tooth-shaped flow guiding components; and gaps between the absorbent paper positioning columns and the inner wall faces of the waste liquid pools a form air channels of the waste liquid pools a.

As a further improvement of the present invention, third waste liquid cavity includes a waste liquid pool b, a middle cover plate b covering an open end of the waste liquid pool b and an upper cover plate b covering the middle cover plate b, wherein the middle cover plate b has a surface facing the upper cover plate b and provided with an absorbent paper assembling groove b, air outlets a are formed in a bottom of the absorbent paper assembling groove b, and air outlets b are formed in a surface, opposite to an opening of the absorbent paper assembling groove b, of the upper cover plate b in a penetration mode.

Another technical purpose of the invention is to provide the chip body is of a three-piece structure and sequentially includes an upper chip layer, a middle chip layer and a lower chip layer from top to bottom, the lower chip layer is provided with a whole blood filter pool, reaction-quantification pools and waste liquid pools, the middle chip layer is provided with a sample inlet groove at a position corresponding to the whole blood filter pool, middle reaction pool through holes at positions corresponding to the reaction-quantification pools, and middle cover plates, used for covering open ends of the waste liquid pools, at positions corresponding to the waste liquid pools; the upper chip layer is provided with a sample inlet groove outer ring at a position corresponding to the sample inlet groove, upper reaction pool through holes at positions corresponding to the middle reaction pool through holes, and upper cover plates at positions corresponding to the middle cover plates; characterized in that three said waste liquid pools are separately disposed on a periphery of the chip body in a semi-enclosure mode and include a first waste liquid pool and a second waste liquid pool located on two sides of the chip body and a third waste fluid pool communicated with the first waste liquid pool and the second waste liquid pool;

the lower chip layer is further provided with a fluid path distribution pool disposed at a middle position of the lower chip layer, a sample delivery branch is disposed between one end of the fluid path distribution pool and the whole blood filter pool, and an external fluid delivery branch is disposed between another end of the fluid path distribution pool and an external fluid path;

the fluid path distribution pool is communicated with either the sample delivery branch or the external fluid delivery branch through a fluid inflow mechanism; the fluid inflow mechanism includes a sample fluid inflow passage, a sample slow flow passage, a distribution cavity fluid inflow passage, an external fluid slow flow passage and an external fluid inflow passage, wherein the sample fluid inflow passage and the external fluid inflow passage are ascending passages, the distribution cavity fluid inflow passage is a descending passage, a fluid inlet of the sample fluid inflow passage is communicated with a fluid inflow cavity through the sample delivery passage, a fluid outlet of the sample fluid inflow passage is communicated with the fluid path distribution cavity sequentially through the sample slow flow passage and the distribution cavity fluid inflow passage, a fluid inlet of the external fluid inflow passage is communicated with the external fluid path through the external fluid delivery passage, and another end of the external fluid inflow passage is communicated with the fluid path distribution cavity sequentially through the external fluid slow flow passage and the distribution cavity fluid inflow passage;

the distribution cavity fluid inflow passage is formed by embedding a plug in a fluid inflow component groove including an isosceles triangle-shaped groove and a cylindrical outer sleeve, the isosceles triangle-shaped groove is reversely disposed, and the cylindrical outer sleeve is disposed along a center line of the isosceles triangle-shaped groove, starts from a bottom edge of the isosceles triangle-shaped groove and extends out of a vertex of the isosceles triangle-shaped groove, so that a circular fluid outflow duct of the distribution cavity fluid inflow passage is formed; the plug is provided with a cylindrical end cap matched with the cylindrical outer sleeve and symmetrically, with respect to a center line of the cylindrical end cap, provided with two oblique outer wall faces forming oblique fluid inflow passages respectively together with two equal oblique sides of the isosceles triangle-shaped groove; one said oblique fluid inflow passage is communicated with the sample slow flow passage, and the other said oblique fluid inflow passage is communicated with the external fluid slow flow passage;

each of two sides of a connecting line between the sample delivery branch and the external fluid delivery branch of the fluid path distribution pool is symmetrically provided with five fluid path branches, each said fluid path branch is connected to one said reaction-quantification pool, and an anti-backflow device is disposed between each said fluid path branch and the corresponding reaction-quantification pool connected with the fluid path branch; moreover, the reaction-quantification pools on two sides of the fluid path distribution pool are disposed in rows to form a first row of reaction-quantification pools and a second row of reaction-quantification pools respectively; the first fluid pool is communicated with the first row of reaction-quantification pools, and the second waste liquid pool is communicated with the second row of reaction-quantification pools;

the first waste liquid pool and the second waste liquid pool are of a same structure; the first waste liquid pool is provided with a middle cover plate having a surface facing the first waste liquid pool and provided with an absorbent paper groove a for accommodating absorbent paper as well as an upper cover plate having a surface facing the first waste liquid pool and provided with conductive sealing ring grooves distributed at intervals, and conductive sealing rings are disposed in the conductive sealing ring grooves; the upper cover plate of the first waste liquid pool is further provided with capacitance probe penetration holes and pressing mechanism head penetration holes at positions corresponding to the conductive sealing ring grooves;

an absorbent paper assembling groove b is formed in a surface, towards an upper cover plate of the third waste liquid pool, of a middle cover plate of the third waste liquid pool; and air holes a are formed in a bottom of the absorbent paper assembling groove b, and air outlets b are formed in a surface, opposite to an opening of the absorbent paper assembling groove b, of the upper cover plate of the third waste liquid pool in a penetration mode.

Another technical objective of the present invention is to provide a multi-flux micro-fluidic chip based on active fluid flow control.

Based on the above-mentioned technical scheme, the present invention has the following advantages over the prior art:

1. One fluid path is evenly divided into ten fluid path branches creatively so that ten items can be detected at the same time, thus, greatly improving the flux of the fluidic-chip.

2. The valve devices and anti-backflow devices creatively designed by the company are adopted and cooperate with the air path for providing forward thrust for fluid so that the fluid velocity in the passages can be controlled at will, and incubation reaction can be conducted in a certain fixed area, and thus true micro-fluidic can be achieved.

3. Quantitative sample adding in a specific sense is achieved by the present invention through the quantification groove.

4. Multiple micro-fluidic chips can be operated by one instrument at the same time, and thus, the flux can be improved, and time can be saved.

BRIEF DESCRIPTION OF THE SEVERAL VIEWS OF THE DRAWINGS

In FIG. 1: 1, upper chip layer; 2, middle chip layer; 3, lower chip layer; 4, air path device; 5-1, pressing mechanism; 5-2, capacitance probe; 5-3, conductive sealing ring; 6, fluid path device; 7-1, third absorbent paper; 7-2, second absorbent paper; 7-3, first absorbent paper; 8, blood filter paper;

In FIG. 2: 5, valve device; 9-3, air path connector; 9-2, sample adding hole; 9-1, air hole; 10, external chip positioning part; 11, reaction-quantification cavity; 12, air outlet; 13, fluid path connector; 14, capacitance probe detection port;

In FIGS. 3, 4a and 4b: 3-1, reaction-quantification pool; 3-2, whole blood filter pool; 3-2-1, side wall of whole blood filter pool; 3-3, second waste liquid pool; 3-1-1, sawtooth-shaped flow guiding components on the inner side wall of second waste liquid pool; 3-4, first waste liquid pool; 3-4-1, absorbent paper fixing component of first waste liquid pool; 3-4-2, sawtooth-shaped flow guiding components on the inner side wall of first waste liquid pool; 3-5, third waste liquid pool; 3-6, chip fixing column; 3-7, fluid path distribution pool;

In FIG. 5: 3-7, fluid path distribution pool; 3-7-1, sample delivery passage; 3-7-2 to 3-7-11, 10 parallel fluid path branches of distribution pool; 3-7-12, external fluid (cleaning solution and chromogenic reagent) delivery passage;

In FIG. 6: 3-1-1, coated antibody storage pool; 3-1-2, labeled antibody storage pool; 3-1-3, reaction pool fluid inflow branch; 3-1-4, reaction pool fluid outflow branch;

In FIGS. 7-8: 2-1, a sample inlet groove; 2-2, conductive sealing ring groove; 2-3, anti-backflow fluid outlet; 2-4, fluid inflow part of fluid path distribution pool; 2-4-1, sample fluid inflow passage; 2-4-2, sample slow flow passage; 2-4-3, distribution cavity fluid inflow passage; 2-4-4, external fluid slow flow passage; 2-4-5, external fluid inflow passage; 2-5, absorbent paper assembling groove; 2-5-1, air outlets in middle chip layer of waste liquid pool; 2-6, through hole of quantification-reaction pool; 2-7, chip fixing column hole;

In FIGS. 9a, 9b and 9c: 1-1, sample inlet groove outer ring; 1-2, capacitance probe penetration hole; 1-3, quantification-reaction pool cover plate; 1-4, pressing mechanism penetration hole; 1-5, air outlet in upper chip layer of waste liquid pool; 1-6, fluid inflow component of fluid path distribution pool;

In FIGS. 10a and 10b: 1-2, capacitance probe penetration hole; 2-2, conductive sealing ring groove; 2-2-1, absorbent paper groove in left waste liquid pool; 3-4, left waste liquid pool;

DETAILED DESCRIPTION OF THE INVENTION

A clear and complete description of the technical scheme of the embodiments of the present invention is given as follows in combination with the drawings in the embodiments. Obviously, the embodiments in the following description are only part of embodiments of the present invention instead of being all embodiments of the present invention. The following description of at least one embodiment by a typical example is actually illustrative solely and is by no means restrictive to the present invention and application or use of the present invention. All other embodiments obtained based on the embodiments of the present invention by those ordinarily skilled in this field without creative work should fall within the protection scope of the present invention. Without additional specifications, relative configurations of components and steps, expressions and numerical values mentioned in these embodiments do not limit the scope of the present invention. Meanwhile, it would appreciate that for a brief description, the components in these figures are drawn not to an actual scale. Techniques, methods and devices known by those ordinarily skilled in relevant fields will possibly not be discussed in detail anymore hereinafter; however, where appropriate, these techniques, methods and devices should be regarded as part of this authorized specification. In all these provided and discussed embodiments, any concrete values should be interpreted as illustrative solely instead of being interpreted as restrictive. Thus, different values are available in other illustrative embodiments.

For a brief description, spatial relative terms such as 'on', 'above', 'on an upper surface' and 'upper' may be used here to explain spatial position relations between one device or characteristic and the other device or characteristic shown in the figures. It would appreciate that these spatial relative terms are intended to include different positions except the position of the device in the figures in service or operation. For instance, if devices in the figures are reversed, the description should be 'on a lower portion of the other device or configuration' or 'below the other device or configuration' based on a previous description 'on an upper portion of the other device or configuration' or 'above the other device or configuration'. Thus, the illustrative term 'above' may include a position 'above' and a position 'below'. The devices can also be positioned in other different ways (rotated by 90° or located at other position).

This invention is disclosed a multi-flux micro-fluidic chip based on active fluid flow control, including a chip body, wherein the chip body includes a fluid inflow cavity, reaction-quantification cavities, fluid path distribution cavity and waste liquid cavities, the fluid path distribution cavity is provided with a sample fluid inlet, an external fluid inlet and a plurality of fluid outlets, wherein the sample fluid inlet of the fluid path distribution cavity is communicated with the fluid inflow cavity through the sample delivery passage, the external fluid inlet of the fluid path distribution cavity is communicated with the external fluid path through the external fluid delivery passage, and the fluid outlets of the fluid path distribution cavity are communicated with the reaction-quantification cavities through the respective fluid path branches; and the fluid path branches are symmetrically distributed on two sides of a connecting line between the sample fluid inlet and the external fluid inlet of the fluid path distribution cavity, and each said fluid path branch has a passage width and a passage length in inverse proportion.

The fluid inlet of the fluid path distribution cavity is communicated with either the fluid inflow cavity or the external fluid path through a fluid inflow mechanism; and the fluid inflow mechanism includes a sample fluid inflow passage, a sample slow flow passage, a distribution cavity fluid inflow passage, an external fluid slow flow passage and an external fluid inflow passage, wherein the sample fluid inflow passage and the external fluid inflow passage are ascending passages, the distribution cavity fluid inflow passage is a descending passage, a fluid inlet of the sample fluid inflow passage is communicated with the fluid inflow cavity through a sample delivery passage, a fluid outlet of the sample fluid inflow passage is communicated with the fluid path distribution cavity sequentially through the sample slow flow passage and the distribution cavity fluid inflow passage, a fluid inlet of the external fluid inflow passage is communicated with the external fluid path through an external fluid delivery passage, and another end of the external fluid inflow passage is communicated with the fluid path distribution cavity sequentially through the external fluid slow flow passage and the distribution cavity fluid inflow passage.

The distribution cavity fluid inflow passage is formed by embedding a plug in a fluid inflow component groove including an isosceles triangle-shaped groove and a cylindrical outer sleeve, the isosceles triangle-shaped groove is reversely disposed, and the cylindrical outer sleeve is disposed along a center line of the isosceles triangle-shaped groove, starts from a bottom edge of the isosceles triangle-shaped groove and extends out of a vertex of the isosceles triangle-shaped groove, so that a circular fluid outflow duct of the distribution cavity fluid inflow passage is formed; the plug is provided with a cylindrical end cap matched with the cylindrical outer sleeve and symmetrically, with respect to a center line of the cylindrical end cap, provided with two oblique outer wall faces forming oblique fluid inflow passages respectively together with two equal oblique sides of the isosceles triangle-shaped groove; and one said oblique fluid inflow passage is communicated with the sample slow flow passage, and the other said oblique fluid inflow passage is communicated with the external fluid slow flow passage.

A fluid path distribution cavity of the present invention is communicated with either reaction-quantification cavities or an external fluid path, wherein:

the number of the reaction-quantification cavities is four or more; in these figures, ten reaction-quantification cavities are separately distributed on two sides of the fluid path distribution cavities in two rows to form a first row of reaction-quantification cavities and a second row of reaction-quantification cavities respectively; and the reaction-quantification cavities are communicated with fluid outlets of the fluid path distribution cavity through respective fluid path branches. In addition, each reaction-quantification cavity includes labeled antibody storage cavities and a coated antibody storage cavity, each said coated antibody storage cavity is disposed at a middle position of the corresponding reaction-quantification cavity and provided with a reaction pool fluid inflow branch and a reaction pool fluid outflow branch, and each of two sides of a connecting line between the reaction pool fluid inflow branch and the reaction pool fluid outflow branch of each said reaction-quantification cavity is provided with one said labeled antibody storage cavity.

The first waste liquid cavity and the second waste liquid cavity are of a same structure and each include a waste liquid pool a, a middle cover plate a covering the waste liquid pool a and an upper cover plate a covering the middle cover plate a, each said middle cover plate a has a surface facing the corresponding waste liquid pool a and provided with an absorbent paper groove a for accommodating absorbent paper as well as a surface facing the corresponding upper cover plate a and provided with a plurality of conductive sealing ring grooves distributed at intervals, and the conductive sealing rings are disposed in the conductive sealing ring grooves; each said upper cover plate a is provided with capacitance probe penetration holes and pressing mechanism head penetration holes at positions corresponding to the conductive sealing ring grooves; a plurality of tooth-shaped flow guiding components are disposed on an inner wall face of each said waste liquid pool a at intervals, and absorbent paper positioning columns are disposed at positions close to tips of the tooth-shaped flow guiding components; and gaps between the absorbent paper positioning columns and the inner wall faces of the waste liquid pools a form air channels of the waste liquid pools a.

The third waste liquid cavity includes a waste liquid pool b, a middle cover plate b covering an open end of the waste liquid pool b and an upper cover plate b covering the middle cover plate b, wherein the middle cover plate b has a surface facing the upper cover plate b and provided with an absorbent paper assembling groove b, air outlets a are formed in a bottom of the absorbent paper assembling groove b, and air outlets b are formed in a surface, opposite to an opening of the absorbent paper assembling groove b, of the upper cover plate b in a penetration mode.

A valve device is disposed on a micro-fluidic passage between each said reaction-quantification cavity and the corresponding waste liquid cavity. Please refer to Chinese Patent Application No. 2017102131082 for a specific description of the valve devices adopted by the present invention. Each valve device includes:

a detection mechanism used for sensing whether or not fluid flows through a valve device mounting position, a pressing mechanism and a sealing component;

the valve devices in a normally open state in the chip body automatically close to be in an interruption state when numerical values fed back by the corresponding detection mechanisms indicate that fluid flows through the corresponding valve device mounting positions;

the valve devices in the interruption state are regularly opened to be in a circulation state;

when the valve devices are in the circulation state, fluid is pushed by air flow from the air path to circulate in the valve devices;

each said sealing component is a conductive sealing ring and includes an outer sealing ring, an inner sealing film located on an inner ring of the outer sealing ring and a probe contact connected with the outer sealing ring;

each said pressing mechanism includes a pressing head located above the corresponding inner sealing film;

each said detection mechanism includes a detection probe which is in linking connection with the corresponding pressing head and located above the corresponding probe contact, and a distance from each said detection probe to the corresponding probe contact is smaller than a distance from each said pressing head to the corresponding inner sealing film;

the micro-fluidic passage at each said valve device mounting position is transversely partitioned by a micro-fluidic passage partition into a micro-valve fluid inflow section and a micro-valve fluid outflow section;

each said micro-valve fluid inflow section is provided with a fluid outlet, and each said micro-valve fluid outflow section is provided with a fluid inlet;

each said inner sealing film is capable of covering the fluid outlet of the corresponding micro-valve fluid inflow section and the fluid inlet of the corresponding micro-valve fluid outflow section at the same time and is sealed by the corresponding outer sealing ring;

when the pressing heads of the pressing mechanisms drive the detection probes to descend towards the conductive sealing rings, the pressing mechanisms stop descending when the detection probes make contact with the probe contacts, and at this moment, gaps exist between the pressing heads and the inner sealing films; when data sensed by the detection probes change, it indicates that fluid flows through the micro-fluidic passages at the valve device mounting positions, the pressing mechanisms are triggered to work to push the pressing heads to continue to descend till the pressing heads press against the inner sealing films to cover the fluid outlets of the micro-valve fluid inflow sections and the fluid inlets of the micro-valve fluid outflow sections at the same time, and the valve devices are in the interruption state at this moment; and when gaps exist between the pressing heads of the pressing mechanisms and the inner sealing films, the valve devices are in an open state, and as the inner sealing films are deformable, it is ensured that fluid flows out from the fluid outlets of the micro-valve fluid inflow sections and flows in from the fluid inlets of the micro-valve fluid outflow sections.

In this invention, an anti-backflow device disposed on the fluid path branch between each reaction-quantification cavity and the fluid path distribution cavity. Please refer to Chinese Patent Application No. 2017102133849 for a detailed description of the anti-backflow devices adopted by the present invention. Each anti-backflow device includes a micro-fluidic passage and an anti-backflow structure. When the micro-fluidic passage is communicated with the external air path, fluid in the micro-fluidic passage through both sides of each said anti-backflow device is driven by air from the external air path to circulate by overcoming a pressure generated by the liquid level, increased by the corresponding anti-backflow passage at the corresponding anti-backflow structure mounting position, of the micro-fluidic passage.

The extension direction of an anti-backflow passage is perpendicular to the extension direction of a micro-fluidic passage at an anti-backflow structure mounting position. The micro-fluidic passage at the anti-backflow structure mounting position is partitioned by a micro-fluidic passage partition block into two sections, namely a micro-fluidic fluid inflow passage and a micro-fluidic fluid outflow passage. The anti-backflow passage has a closed upper end and a lower end stretching over the micro-fluidic passage partition block, and the upper end and the lower end of the anti-backflow passage are respectively communicated with the micro-fluidic fluid inflow passage and the micro-fluidic fluid outflow passage.

An anti-backflow protrusion is disposed in the anti-backflow passage, and two anti-backflow communication passages are formed between the anti-backflow protrusion and the anti-backflow passage and respectively communicated with the micro-fluidic fluid inflow passage and the micro-fluidic fluid outflow passage. The anti-backflow protrusion has a lower end flush with the lower end of the anti-backflow passages and an upper end lower than the upper end of the anti-backflow passages.

The anti-backflow protrusion between the two anti-backflow communication passages has a trapezoidal section.

The micro-fluidic passage partition block is a wedge block, and the anti-backflow passage is a wedge groove matched with the micro-fluidic passage partition block in shape.

The micro-fluidic passage at the anti-backflow structure mounting position is symmetrically provided with wedge-shaped connection columns on both sides of the micro-fluidic passage partition block. The anti-backflow passage is provided with wedge-shaped connection grooves cooperatively connected with the wedge-shaped connection columns.

In this invention, fluid inflow cavity can be referred to Chinese Patent Application No. 2017103771423. The whole blood filter cavity includes a whole blood sample filter tank and a top cover for sealing the whole blood sample filter tank, and the sample inlet part is disposed on the top cover; the whole blood sample filter tank is provided with a filtered sample outlet and has a side wall extending to the filtered sample outlet in a gradually converging mode, and the side wall extending in the gradually converging mode is provided with teeth used for guiding flow; and whole blood sample filter paper is laid in the whole blood sample filter tank, and a side edge of the whole blood sample filter paper makes contact with internal tips of the adjacent teeth on the tooth-shaped side wall of the whole blood sample filter cavity.

A detailed embodiment based on the technical scheme of the present invention is disclosed with the accompanying drawings. A multi-flux micro-fluidic chip based on active fluid flow control, as shown in FIG. 1 to FIG. 12, the chip body is of a three-piece structure and sequentially includes an upper chip layer, a middle chip layer and a lower chip layer from top to bottom.

Figure 1:
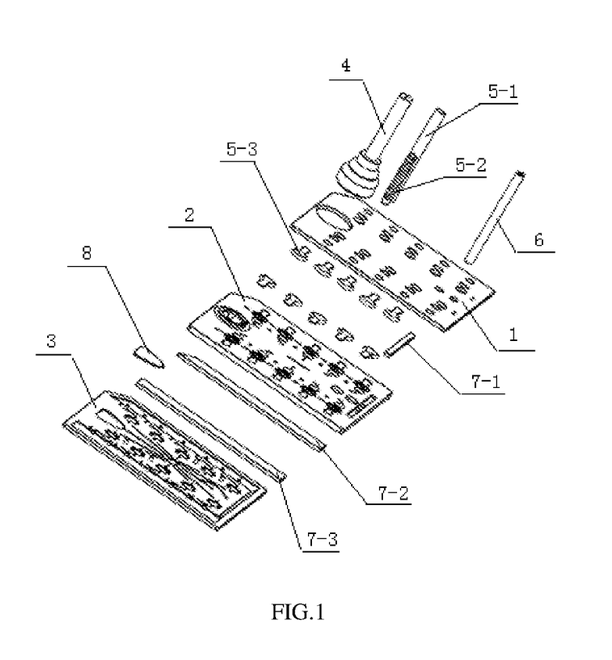
FIG. 1 is a structural view of a micro-fluidic chip based on active fluid flow control of the present invention.
Figure 2:
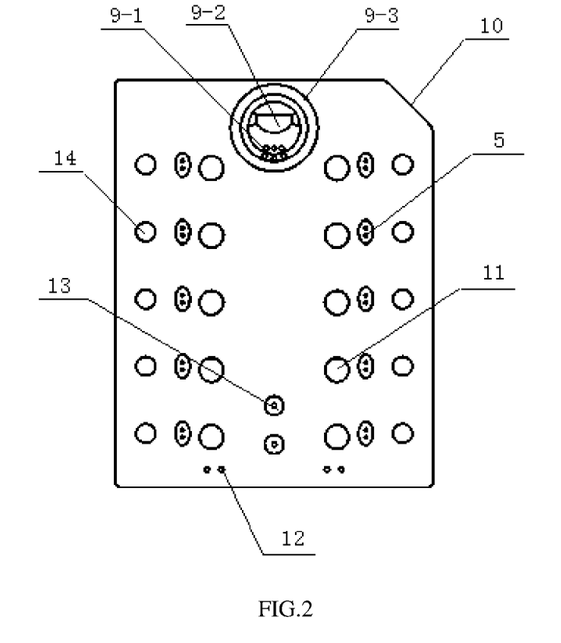
FIG. 2 is a top view of a micro-fluidic chip of the present invention.
Figure 3:
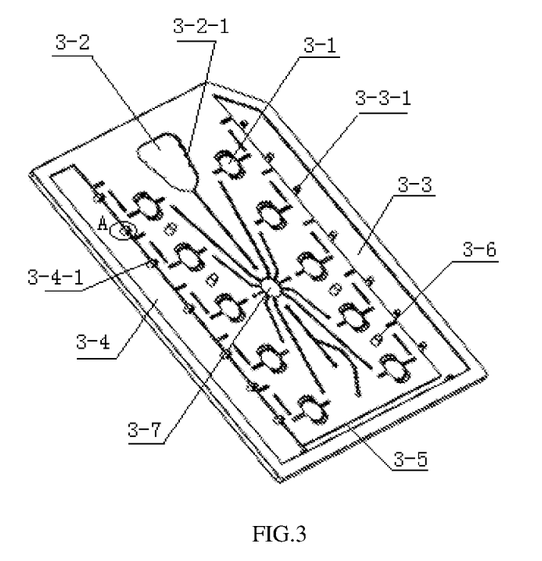
FIG. 3 is a structural view of a lower chip layer of the present invention.
Figure 4A:
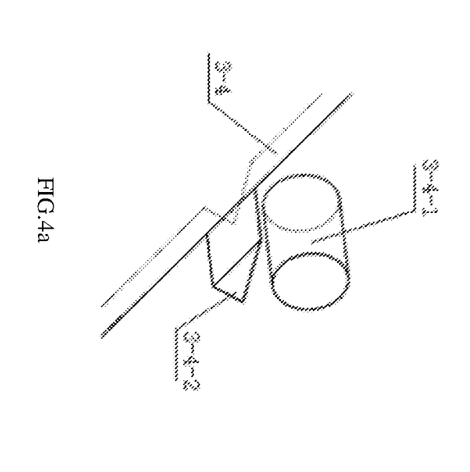
FIG. 4a is an enlarged view of part A in FIG. 3.
Figure 4B:
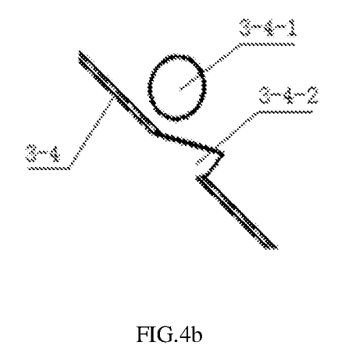
FIG. 4b is a top view of part A in FIG. 3.

As shown in FIG. 3, FIG. 4a and FIG. 4b, the lower chip layer is provided with a whole blood filter pool, reaction-quantification pools and waste liquid pools.

Three said waste liquid pools are separately disposed on a periphery of the chip body in a semi-enclosure mode and include a first waste liquid pool and a second waste liquid pool located on two sides of the chip body and a third waste liquid pool communicated with the first waste liquid pool and the second waste liquid pool.

The lower chip layer is further provided with a fluid path distribution pool disposed at a middle position of the lower chip layer, a sample delivery branch is disposed between one end of the fluid path distribution pool and the whole blood filter pool, and an external fluid delivery branch is disposed between another end of the fluid path distribution pool and an external fluid path. Specifically, the embodiment is used for delivering a cleaning solution or a chromogenic reagent.

Figure 5:
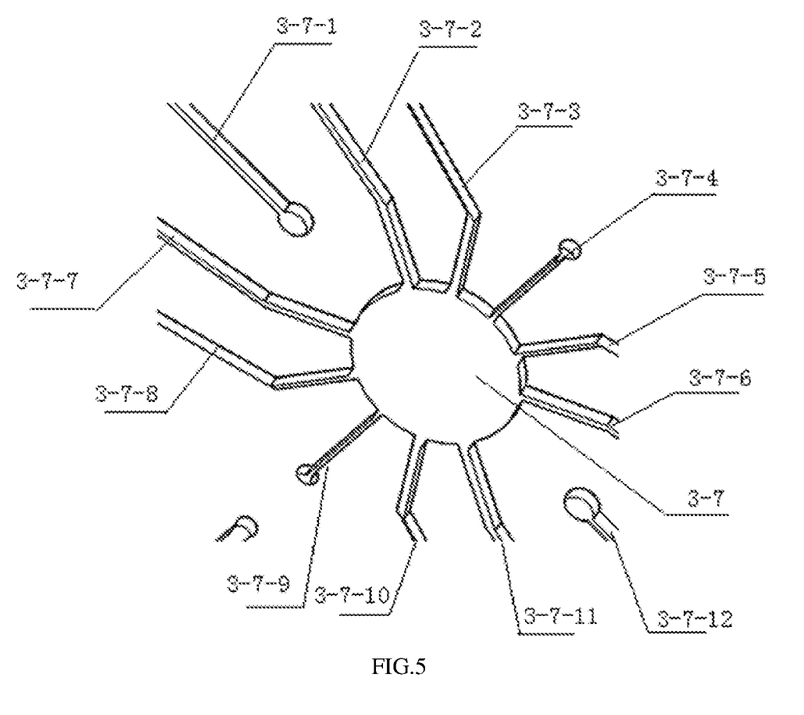
FIG. 5 is an enlarged view of a fluid path distribution pool of the present invention.

As shown in FIG. 5, fluid path distribution pool has ten parallel fluid path branches of distribution pool, each of two sides of a connecting line between the sample delivery branch and the external fluid delivery branch of the fluid path distribution pool is symmetrically provided with five fluid path branches, each said fluid path branch is connected to one said reaction-quantification pool, and an anti-backflow device is disposed between each said fluid path branch and the corresponding reaction-quantification pool connected with the fluid path branch.

Figure 6:
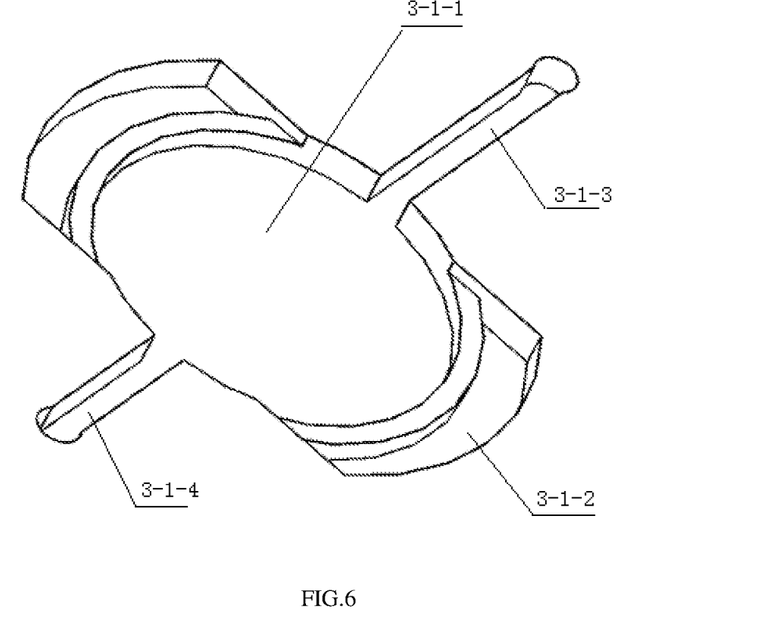
FIG. 6 is an enlarged view of a quantification-reaction pool.

As shown in FIG. 6, each reaction-quantification cavity includes labeled antibody storage pools and a coated antibody storage pool, wherein the coated antibody storage pool is disposed at a middle position of the reaction-quantification cavity and provided with a reaction pool fluid inflow branch and a reaction pool fluid outflow pool, and each of two sides of a connecting line between the reaction pool fluid inflow branch and the reaction pool fluid outflow pool is provided with one labeled antibody storage pool.

Figure 7:
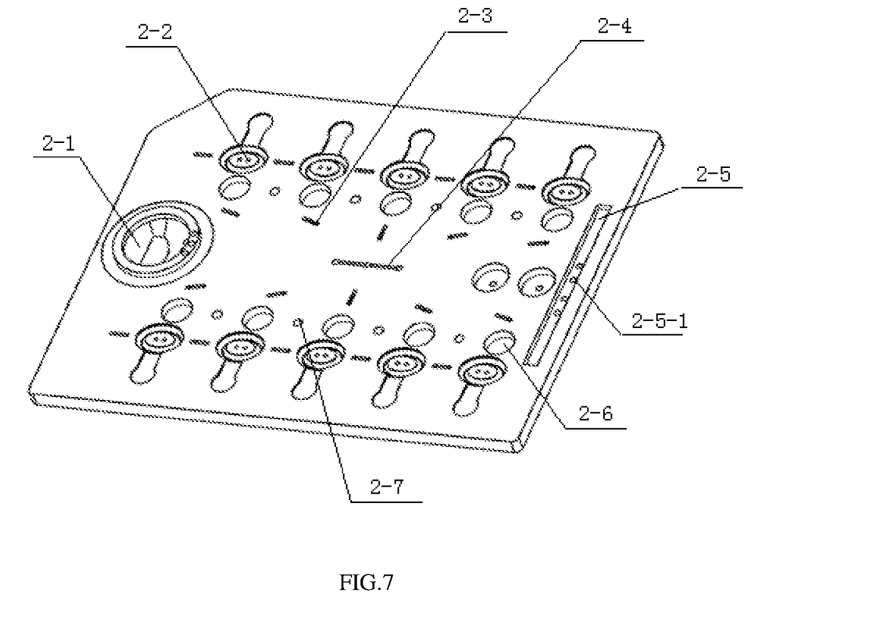
FIG. 7 is a structural view of a middle chip layer.
Figure 8:
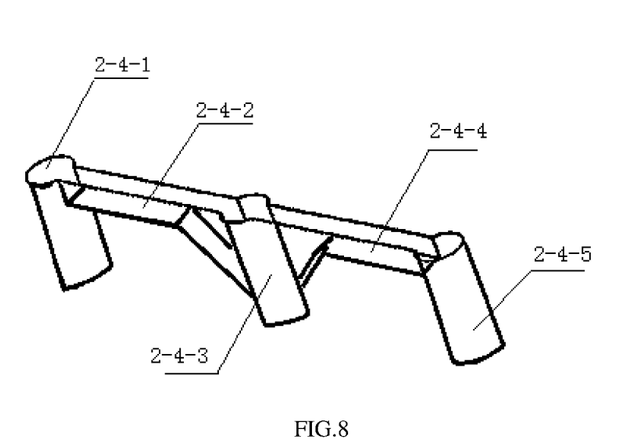
FIG. 8 is a structural view of a fluid inflow part of a fluid path distribution pool.

As shown in FIG. 7, the middle chip layer is provided with a sample inlet groove at a position corresponding to the whole blood filter pool, middle reaction pool through holes at positions corresponding to the reaction-quantification pools, and middle cover plates, used for covering open ends of the waste liquid pools, at positions corresponding to the waste liquid pools.

Figure 9A:
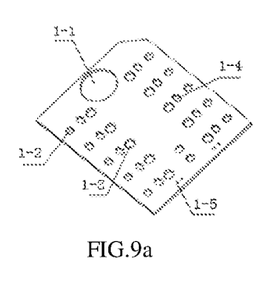
FIG. 9a is a top view of an upper chip layer.
Figure 9B:
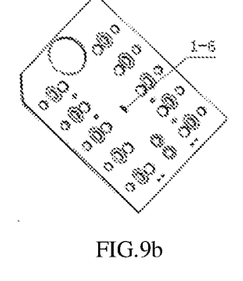
FIG. 9b is a bottom view of an upper chip layer.
Figure 9C:
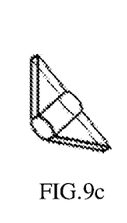
FIG. 9c is a structural view of a fluid inflow part of a fluid path distribution pool.
Figure 10A:
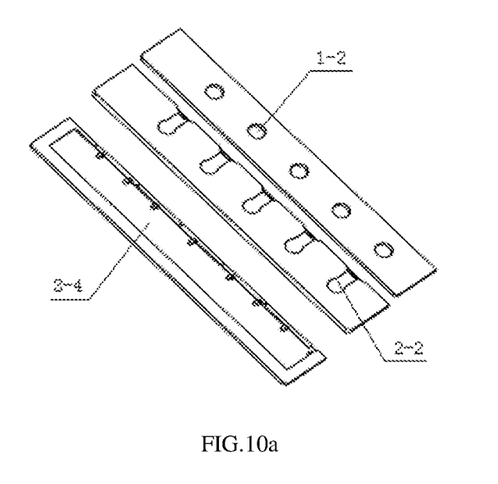
FIG. 10a is a structural view of a left waste liquid cavity in one direction.
Figure 10B:
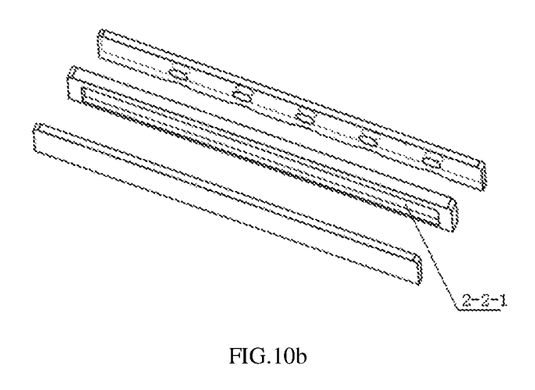
FIG. 10b is a structural view of the left waste liquid cavity in another direction.
Figure 11A:
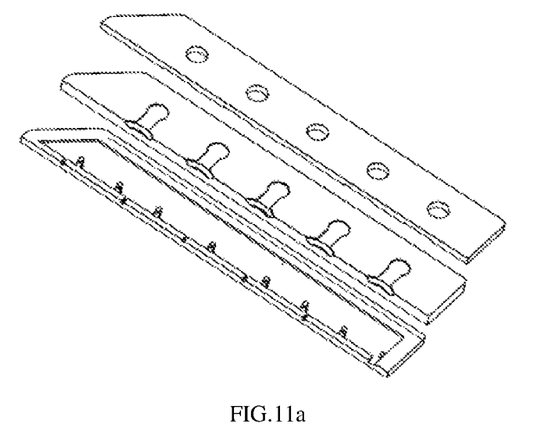
FIG. 11a is a structural view of a right waste liquid cavity of the present invention.
Figure 11B:
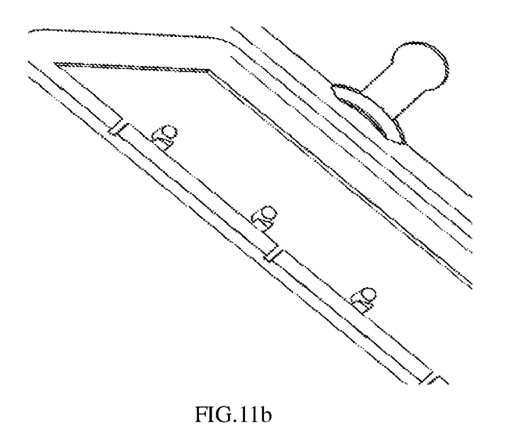
FIG. 11b is a partial enlarged view of the right waste liquid cavity.
Figure 11C:
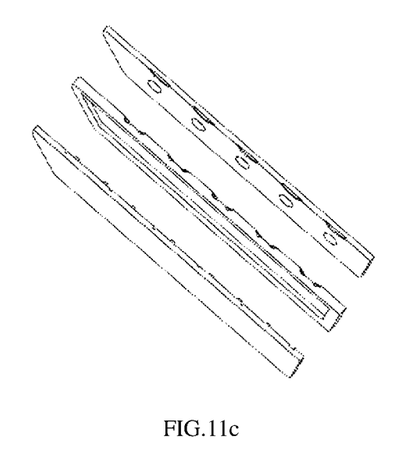
FIG. 11c is a structural view of the right waste liquid cavity in another direction.

As shown in FIG. 9a, FIG. 9b, FIG. 9c, the upper chip layer is provided with a sample inlet groove outer ring at a position corresponding to the sample inlet groove, upper reaction pool through holes at positions corresponding to the middle reaction pool through holes, and upper cover plates at positions corresponding to the middle cover plates.

As shown in FIG. 10a, FIG. 10b and FIG. 11a to 11c, the first waste liquid pool and the second waste liquid pool are of a same structure; the first waste liquid pool is provided with a middle cover plate having a surface facing the first waste liquid pool and provided with an absorbent paper groove a for accommodating absorbent paper as well as an upper cover plate having a surface facing the first waste liquid pool and provided with conductive sealing ring grooves distributed at intervals, and conductive sealing rings are disposed in the conductive sealing ring grooves; the upper cover plate of the first waste liquid pool is further provided with capacitance probe penetration holes and pressing mechanism head penetration holes at positions corresponding to the conductive sealing ring grooves.

Figure 12:
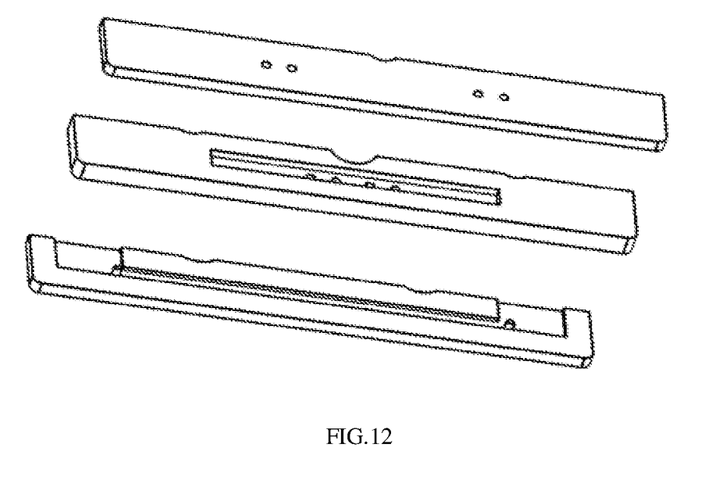
FIG. 12 is a structural view of a front waste liquid cavity.

As shown in FIG. 12, an absorbent paper assembling groove b is formed in a surface, towards an upper cover plate of the third waste liquid pool, of a middle cover plate of the third waste liquid pool; and air holes a are formed in a bottom of the absorbent paper assembling groove b, and air outlets b are formed in a surface, opposite to an opening of the absorbent paper assembling groove b, of the upper cover plate of the third waste liquid pool in a penetration mode.

The fluid path distribution pool of the present invention has the following characteristics:

A. One fluid path is evenly divided into ten fluid path branches.

B. The passage width is in inverse proportion with the passage length to balance the fluid flow resistance.

C. Fluid flows downwards from the middle circle to be evenly distributed into ten passages.

D. Resistance (anti-backflow) devices for making fluid flow upwards are additionally disposed at tail ends of the ten passages, so that differences between the passages are further eliminated.

Each reaction-quantification pool of the present invention has the following characteristics:

A coated antibody is physically separated from labeled antibodies, so that specific binding of the coated antibody and the labeled antibodies is effectively avoided, and the signal to noise ratio is improved. Meanwhile, the coated antibody and the labeled antibodies are located in the same pool, so that chip design is easy and convenient.

The design of the first waste liquid pool and the second waste liquid pool has the following characteristics:

A. The absorbent paper absorbs fluid to prevent fluid leakage.

B. The absorbent paper fixing columns and the tooth-shaped flow guiding components are arranged to prevent the waste liquid pools from being completely filled with the absorbent paper, and air channels are reserved to prevent fluid in the absorbent paper from being blown out.

C. The sawtooth-shaped flow guiding components prevent fluid from flowing out from the air channels.

D. The volumes of the waste liquid pools are increased by middle chip layer segments in the waste liquid pools.

The design of the third waste liquid pool has the following characteristics:

A. The absorbent paper on the middle chip layer eliminates possible fluid leakage and bubble seepage.

B. The air outlets in the middle chip layer and the upper chip layer further eliminate possible fluid leakage and bubble seepage.

In conclusion, the present invention has the following advantages:

The fluid path uniform distribution device is designed to improve the flux of the micro-fluidic chip.

The valve devices and the anti-backflow devices are creatively designed and cooperate with the air path for providing forwards thrust for fluid so that the fluid velocity in the passages can be controlled at will; and incubation reaction can be conducted in a certain fixed area to achieve true micro-fluidic.

Absorbent materials are additionally disposed in the waste liquid pools to prevent waste liquid from splashing outwards; and the air channels, the sawtooth-shaped flow guiding components and the absorbent paper on the middle chip layer are ingeniously designed to effectively avoid fluid leakage, and the production process can be made simple and practical.

The sealing rings made from conductive rubber and the capacitance detection probes are used to detect the flow state of fluid.

A quantification groove, a labeled antibody groove and a reaction groove are combined to achieve effective quantitative sample adding; and the labeled antibodies and the coated antibody are placed in different areas of the same groove, so that specific binding is effectively avoided, the signal to noise ratio is improved, and the design is simple and practical.

The fluid path is connected with the chip to clean the reaction groove, so that the reaction cost can be effectively reduced, and chip sensitivity can be improved.

What is claimed is:

1. A multi-flux micro-fluidic chip based on active fluid flow control, including a chip body, wherein the chip body includes a fluid inflow cavity, reaction-quantification cavities and waste liquid cavities, and the fluid inflow cavity is communicated with an external air path; characterized in that the multi-flux micro-fluidic chip based on active fluid flow control further includes a fluid path distribution cavity disposed at a middle position of the chip body; the number of the reaction-quantification cavities is four or more, and the four or more reaction-quantification cavities are distributed on two sides of the fluid path distribution cavity in rows to form a first row of reaction-quantification cavities and a second row of reaction-quantification cavities respectively; and the reaction-quantification cavities are communicated with a fluid outlet of the fluid path distribution cavity through respective fluid path branches, and a fluid inlet of the fluid path distribution cavity is communicated with a fluid outlet of the fluid inflow cavity and an external fluid path; the waste liquid cavities include a first waste liquid cavity, a second waste liquid cavity and a third waste liquid cavity and three said waste liquid cavities are separately disposed on a periphery of the chip body in a semi-enclosed mode, wherein the first waste liquid cavity and the second waste liquid cavity are located on two sides of the chip body, the third waste liquid cavity is communicated with the first waste liquid cavity and the second waste liquid cavity, the first waste liquid cavity is communicated with the first row of the reaction-quantification cavities, and the second waste fluid cavity is communicated with the second row of reaction-quantification cavities; the third waste liquid cavity includes a waste liquid pool b, a middle cover plate b covering an open end of the waste liquid pool b and an upper cover plate b covering the middle cover plate b, wherein the middle cover plate b has a surface facing the upper cover plate b and provided with an absorbent paper assembling groove b, air outlets a are formed in a bottom of the absorbent paper assembling groove b, and air outlets b are formed in a surface, opposite to an opening of the absorbent paper assembling groove b, of the upper cover plate b in a penetration mode.

2. The multi-flux micro-fluidic chip based on active fluid flow control according to claim 1, wherein the fluid inlet of the fluid path distribution cavity is communicated with either the fluid inflow cavity or the external fluid path through a fluid inflow mechanism; and the fluid inflow mechanism includes a sample fluid inflow passage, a sample slow flow passage, a distribution cavity fluid inflow passage, an external fluid slow flow passage and an external fluid inflow passage, wherein the sample fluid inflow passage and the external fluid inflow passage are ascending passages, the distribution cavity fluid inflow passage is a descending passage, a fluid inlet of the sample fluid inflow passage is communicated with the fluid inflow cavity through a sample delivery passage, a fluid outlet of the sample fluid inflow passage is communicated with the fluid path distribution cavity sequentially through the sample slow flow passage and the distribution cavity fluid inflow passage, a fluid inlet of the external fluid inflow passage is communicated with the external fluid path through an external fluid delivery passage, and another end of the external fluid inflow passage is communicated with the fluid path distribution cavity sequentially through the external fluid slow flow passage and the distribution cavity fluid inflow passage.

3. The multi-flux micro-fluidic chip based on active fluid flow control according to claim 2, wherein the distribution cavity fluid inflow passage is formed by embedding a plug in a fluid inflow component groove including an isosceles triangle-shaped groove and a cylindrical outer sleeve, the isosceles triangle-shaped groove is reversely disposed, and the cylindrical outer sleeve is disposed along a center line of the isosceles triangle-shaped groove, starts from a bottom edge of the isosceles triangle-shaped groove and extends out of a vertex of the isosceles triangle-shaped groove, so that a circular fluid outflow duct of the distribution cavity fluid inflow passage is formed; the plug is provided with a cylindrical end cap matched with the cylindrical outer sleeve and symmetrically, with respect to a center line of the cylindrical end cap, provided with two oblique outer wall faces forming oblique fluid inflow passages respectively together with two equal oblique sides of the isosceles triangle-shaped groove; and one said oblique fluid inflow passage is communicated with the sample slow flow passage, and the other said oblique fluid inflow passage is communicated with the external fluid slow flow passage.

4. The multi-flux micro-fluidic chip based on active fluid flow control according to claim 1, wherein the fluid path distribution cavity is provided with a sample fluid inlet, an external fluid inlet and a plurality of fluid outlets, wherein the sample fluid inlet of the fluid path distribution cavity is communicated with the fluid inflow cavity through the sample delivery passage, the external fluid inlet of the fluid path distribution cavity is communicated with the external fluid path through the external fluid delivery passage, and the fluid outlets of the fluid path distribution cavity are communicated with the reaction-quantification cavities through the respective fluid path branches; and the fluid path branches are symmetrically distributed on two sides of a connecting line between the sample fluid inlet and the external fluid inlet of the fluid path distribution cavity, and each said fluid path branch has a passage width and a passage length in inverse proportion.

5. The multi-flux micro-fluidic chip based on active fluid flow control according to claim 1, wherein each said reaction-quantification cavity includes labeled antibody storage cavities and a coated antibody storage cavity, each said coated antibody storage cavity is disposed at a middle position of the corresponding reaction-quantification cavity and provided with a reaction pool fluid inflow branch and a reaction pool fluid outflow branch, and each of two sides of a connecting line between the reaction pool fluid inflow branch and the reaction pool fluid outflow branch of each said reaction-quantification cavity is provided with one said labeled antibody storage cavity.

6. The multi-flux micro-fluidic chip based on active fluid flow control according to claim 1, wherein a valve device is disposed on a micro-fluidic passage between each said reaction-quantification cavity and the corresponding waste liquid cavity and includes:
a detection mechanism used for sensing whether or not fluid flows through a valve device mounting position, a pressing mechanism and a sealing component;
the valve devices in a normally open state in the chip body automatically close to be in an interruption state when numerical values fed back by the corresponding detection mechanisms indicate that fluid flows through the corresponding valve device mounting positions;
the valve devices in the interruption state are regularly opened to be in a circulation state;

when the valve devices are in the circulation state, fluid is pushed by air flow from the air path to circulate in the valve devices;

each said sealing component is a conductive sealing ring and includes an outer sealing ring, an inner sealing film located on an inner ring of the outer sealing ring and a probe contact connected with the outer sealing ring;

each said pressing mechanism includes a pressing head located above the corresponding inner sealing film;

each said detection mechanism includes a detection probe which is in linking connection with the corresponding pressing head and located above the corresponding probe contact, and a distance from each said detection probe to the corresponding probe contact is smaller than a distance from each said pressing head to the corresponding inner sealing film;

the micro-fluidic passage at each said valve device mounting position is transversely partitioned by a micro-fluidic passage partition into a micro-valve fluid inflow section and a micro-valve fluid outflow section;

each said micro-valve fluid inflow section is provided with a fluid outlet, and each said micro-valve fluid outflow section is provided with a fluid inlet;

each said inner sealing film is capable of covering the fluid outlet of the corresponding micro-valve fluid inflow section and the fluid inlet of the corresponding micro-valve fluid outflow section at the same time and is sealed by the corresponding outer sealing ring;

when the pressing heads of the pressing mechanisms drive the detection probes to descend towards the conductive sealing rings, the pressing mechanisms stop descending when the detection probes make contact with the probe contacts, and at this moment, gaps exist between the pressing heads and the inner sealing films; when data sensed by the detection probes change, it indicates that fluid flows through the micro-fluidic passages at the valve device mounting positions, the pressing mechanisms are triggered to work to push the pressing heads to continue to descend till the pressing heads press against the inner sealing films to cover the fluid outlets of the micro-valve fluid inflow sections and the fluid inlets of the micro-valve fluid outflow sections at the same time, and the valve devices are in the interruption state at this moment; and when gaps exist between the pressing heads of the pressing mechanisms and the inner sealing films, the valve devices are in an open state, and as the inner sealing films are deformable, it is ensured that fluid flows out from the fluid outlets of the micro-valve fluid inflow sections and flows in from the fluid inlets of the micro-valve fluid outflow sections.

7. The multi-flux micro-fluidic chip based on active fluid flow control according to claim 1, wherein the first waste liquid cavity and the second waste liquid cavity are of a same structure and each include a waste liquid pool a, a middle cover plate a covering the waste liquid pool a and an upper cover plate a covering the middle cover plate a, each said middle cover plate a has a surface facing the corresponding waste liquid pool a and provided with an absorbent paper groove a for accommodating absorbent paper as well as a surface facing the corresponding upper cover plate a and provided with a plurality of conductive sealing ring grooves distributed at intervals, and the conductive sealing rings are disposed in the conductive sealing ring grooves; each said upper cover plate a is provided with capacitance probe penetration holes and pressing mechanism head penetration holes at positions corresponding to the conductive sealing ring grooves; a plurality of tooth-shaped flow guiding components are disposed on an inner wall face of each said waste liquid pool a at intervals, and absorbent paper positioning columns are disposed at positions close to tips of the tooth-shaped flow guiding components; and gaps between the absorbent paper positioning columns and the inner wall faces of the waste liquid pools a form air channels of the waste liquid pools a.

* * * * *